United States Patent [19]

Lezdey et al.

[11] Patent Number: 5,346,886

[45] Date of Patent: Sep. 13, 1994

[54] TOPICAL α-1-ANTITRYPSIN, NON-AQUEOUS LIPID MISCIBLE, BENZALKONIUM CHLORIDE COMPOSITIONS FOR TREATING SKIN

[76] Inventors: John Lezdey, 976 Kingston Dr., Cherry Hill, N.J. 08034; Allan Wachter, 9822 S. Grandview, Tempe, Ariz. 85284

[21] Appl. No.: 151,980

[22] Filed: Nov. 15, 1993

[51] Int. Cl.$^5$ ............... A61K 37/10; A61K 31/135
[52] U.S. Cl. .......................... 514/8; 514/647
[58] Field of Search ...................... 514/8, 647

[56] References Cited

U.S. PATENT DOCUMENTS

| | | | |
|---|---|---|---|
| 5,008,242 | 4/1991 | Lezdey | 514/8 |
| 5,134,119 | 7/1992 | Lezdey | 514/8 |
| 5,166,134 | 11/1992 | Lezdey | 514/8 |
| 5,190,917 | 3/1993 | Lezdey | 514/8 |
| 5,217,951 | 6/1993 | Lezdey | 514/8 |

OTHER PUBLICATIONS

Hubbard et al, "Biochemical Efficacy and Safety of Monthly Augmentation Therapy for Alpha 1-Antitrypsin Deficiency" JAMA, vol. 260, No. 9, Sep. 2, 1988.
Remington Pharmaceutical Sciences p. 730, 1159, 1985.

*Primary Examiner*—Gregory Hook
*Attorney, Agent, or Firm*—John Lezdey

[57] ABSTRACT

The invention provides a pharmaceutical composition for the treatment of a mammal having a skin disease. The composition contains a serine protease inhibitor and an effective amount of a cationic quaternary ammonium salt at a concentration below the critical micelle concentration for increasing the penetration of the inhibitor in the skin. Additionally, these may be included an ethoxylated nonylphenol.

1 Claim, No Drawings

TOPICAL α-1-ANTITRYPSIN, NON-AQUEOUS LIPID MISCIBLE, BENZALKONIUM CHLORIDE COMPOSITIONS FOR TREATING SKIN

FIELD OF THE INVENTION

The present invention relates to pharmaceutical preparations containing serine protease inhibitors for use in topical applications. More particularly, the invention provides preparations for increasing the penetration of serine protease inhibitors when applied to the skin.

BACKGROUND OF THE INVENTION

Topical therapy permits drug application to a specific disease site in high concentrations with little systemic influence. This can yield more efficient dosages which minimizes the potential of side effects.

The percutaneous absorption of a drug varies greatly dependant on numerous factors. Little quantitative data is available on permeation of specific drugs, but there is a general knowledge of the issues which effect permeation of the skin. The principal barrier to permeation is the stratum corneum. It is desirable to provide a topical dosage form which will be physically and chemically stable, cosmetically acceptable to the patient, and adequately/efficiently transport the active drug to the site of action. This is difficult when the drug is a natural protein which degrades when standing over a period of time in warm weather and even at room temperature.

The search for a suitable vehicle for serine protease inhibitors must take into account the following parameters:

1. Compatibility
2. Stability
3. Physiological Inertness
4. Promotion of Bioavailabiity
5. Easy Spreadability
6. Resistance to Microbial Growth
7. Sufficient Capacity
8. Cosmetic Acceptability The ideal vehicle would be one that is very stable and would withstand storage over a considerable period of time and temperature range without deterioration.

The ideal vehicle should be relatively inert pharmacologically and physiologically. An exception is a base that moisturizes or hydrates the dermis and thereby increases penetration. If the vehicle either moisturizes the skin directly or prevents the loss of moisture from the skin, it may enhance permeation of the drug. In this scenario, the physiological action of the vehicle would be desirable and beneficial.

Otherwise, it is important that the vehicle have little or no effect on the skin. It should be free of irritating or sensitizing properties. The ideal vehicle should be nonreactive with the drug itself. In other words the vehicle should not interfere with the bioavailability of the drug and if possible it should promote the absorption of the drug by the base.

The components of the base must be compatible with each other. Surfactants, emulsifying agents, and preservatives must all be compatible with each other as well as with the drug if they are to be used successfully.

For clinical purposes it is advisable to have a vehicle that will remain stable for at least six months, that requires no major compounding at the time of dispensing and will remain stable at a temperature range roughly between 5 and 50 degrees Centigrade.

The vehicle itself should have no physiological action apart from its role of carrying the active ingredient. Ideally, we are seeking an agent that is neither irritating or sensitizing.

If the drug, namely the serine protease inhibitor, is to be effective topically it must be available to penetrate the dermis. This means it must be released by the base or carried with the base across the skin barrier. If the skin is intact, the base may facilitate this action by softening or hydrating the superficial epidermal tissue if that tissue has become dry, cracked or impervious to penetration. Theoretical an ideal base could alter the membrane permeability of the skin. The actual permeability of skin to a number of drugs is accurately correlated with the water solubility and mineral oil/water partition coefficient of the drug. Ionization of the drug is also a very important factor so the pH of both the drug and the vehicle must be taken into consideration.

The efficacy of any topical medication is dependant on the intimate contact of the vehicle and drug with the skin. A vehicle which will not coat or spread evenly is not capable of providing the free and close contact we desire.

Frequently, ointment and cream bases have turned out to be excellent growth mediums for bacteria. This is definitely undesirable and possible contamination of the skin cannot be risked. We need to consider the various antibacterials and preservatives available in light of the characteristics of the drug itself.

It is not only essential that the vehicle meet all of the above qualification, it must be capable of holding a sufficient concentration of the drug in a homogenous state and reasonable volume.

Cosmetic acceptability involves several areas of concern. A topical product should be easily applied to the skin. It is essential that the vehicle be readily spreadable to assure compliance and to avoid irregular concentrations of the drug on the skin because of uneven application of the preparation. The ease of application and removal of the vehicle can determine whether or not the treatment program is adhered to. The frequency of application if another property that must be considered. Properties of the vehicle can determine if the drug must be applied frequently, it may be easily removed by evaporation, friction, etc. A vehicle that requires prolonged soaks or wet dressings can also negatively affect compliance. Vehicles that feel sticky, greasy or slimy, that stain clothes, skin and everything else that is touched are also not acceptable. Additional problems with compliance can occur if the vehicle is not cosmetically pleasant or acceptable to the patient. It is preferable to have a vehicle that not only feels pleasant on the skin, but one that does not bring attention to its use. In this particular context color and odor are very important characteristics.

SUMMARY OF THE INVENTION

According to the present invention there is provided a pharmaceutical vehicle for the topical application of a serine protease inhibitor which permits prolonged activity of the inhibitor at the site of application and improved penetration. The improved penetration is provided with a vehicle comprising a hydrophilic ointment base of petrolatum, mineral oil, mineral wax, wax wool alcohol, water and a cationic quaternary ammonium salt. More specifically the vehicle contains about 20 to 50% by weight of petrolatum, about 5 to 20% by weight of mineral oil, about 0 to 20% by weight of mineral wax, about 0 to 10% by weight of wax wool alcohol, about 1 to 5% by weight of water and about 0,001 to 0.05% by weight of a cationic quaternary ammonium salt, especially, benzalkonium chloride.

The preparation preferably is used to prepare a formulation containing about 2 to 10% by weight of serine protease inhibitor and maintain the surfactant below the critical micelle concentration. It has been surprisingly found that there is a synergism when the cationic quaternary ammonium salt is used in combination with an ethoxylated nonylphenol.

DESCRIPTION OF THE PREFERRED EMBODIMENTS

The present invention provides an improvement in topically applied compositions containing a serine protease inhibitor which is used to treat skin conditions in mammals, for example, atopic dermatitis, psoriasis, contact dermatitis, and the like. More particularly, a cationic quaternary ammonium salt is used to break the surface tension resulting from the carrier and to permit improved penetration of the serine protease inhibitor into the skin. A small amount of the quaternary ammonium salt, is required, preferably about 0.001 to 0.05% by weight of the composition. Surprisingly, the addition of an ethoxylated nonylphenol provides a synergistic effect of greater penetration of the serine protease inhibitor. An amount of about 0.001 to 0.05% by weight of ethoxylated nonylphenol is usually sufficient. However, the combination of quaternary ammonium salt and ethoxylated nonylphenol must be below the critical micelle concentration.

The quaternary ammonium salt has been found to be particularly useful with a vehicle comprising a hydrophilic ointment base of petrolatum, mineral oil, mineral wax, wax wool alcohol and water. A preferred vehicle comprises about 20 to 50% by weight of petrolatum, about 5 to 20% by weight of mineral oil, about 0 to 20% by weight of mineral wax, about 0 to 10% by weight of wool wax alcohol, about 1 to 5% by weight of water, about 0.001 to 0.05% by weight of a cationic quaternary ammonium salt, and optionally, about 0,001 to 0.05% by weight of an ethoxylated nonylphenol.

Illustrative nonoinic surfactants having the desired characteristics for formulation are available on the market under the tradename of "NEODOL" products by Shell Oil Company; "TERGITOL" products by Union Carbide Company; and "ALFOL" products by Continental Oil Company. Specific examples include "NEODOL 25-7" (linear $C_{12}$–$C_{15}$ primary alcohol condensed with 7 moles of ethylene oxide per mole of alcohol); "NEODOL 45-7" (linear $C_{14}$–$C_{15}$ primary alcohol mixture condensed with 7 moles of ethylene oxide per mole of alcohol); "TERGITOL" having the formula $C_9H_{19}C_6H_4(OCH_2CH_2)_nOH$ wherein n is 8 to 10, preferably an average value of 9, and is condensed with 5 to 8 moles of ethylene oxide.

The cationic quaternary ammonium salts which include a greater number of short-chain alkyl groups in the structure, incline toward better properties. Specific examples of such compounds that may be used in the compositions of this invention include di-isobutyl cresoxy ethoxy ethyl dimethyl benzyl ammonium chloride, di-isobutyl phenoxy ethoxy ethyl dimethyl benzyl ammonium chloride, myristyl dimethylbenzene ammonium chloride, benzalkonium chloride, cetyl pyridinium chloride, coconut dimethyl benzyl ammonium chloride, stearyl dimethyl benzyl ammonium chloride, alkyl dimethyl benzyl ammonium chloride, alkyl diethyl benzyl ammonium chloride, alkyl dimethyl benzyl ammonium bromide, di-isobutyl phenoxy ethoxy ethyl trimethyl ammonium chloride, di-isobutyl phenoxy ethoxy ethyl dimethyl alkyl ammonium chloride, methyl-dodecylbenzyl trimethyl ammonium chloride, cetyl trimethyl ammonium bromide, octadecyl dimethyl ethyl ammonium bromide, cetyl dimethyl ethyl ammonium bromide, octadecenyl-9-dimethyl ethyl ammonium bromide, dioctyl dimethyl ammonium chloride, dodecyl trimethyl ammonium chloride, octadecyl trimethyl ammonium chloride, octadecyl trimethyl ammonium bromide, hexadecynyl trimethyl ammonium iodine, octyltrimethyl ammonium fluoride, and mixtures thereof. Other water dispersible salts, such as the acetates, sulfates, nitrates, and phosphates, are effective in place of the halides, but the chlorides and bromides are preferred.

The preferred quaternary ammonium salt for use in the invention is benzalkonium chloride. The amount used is generally about 0,001 to 0.05% by weight of composition. The benzalkonium chloride is commercially available and is sold under the name "BARQUAT or quaternium-15."

The serine protease inhibitors which are contemplated in the present invention are any of the inhibitors, their analogs, derivates or salts of the human type which can inhibit mast cells or bind with any one or more of the protease derived from eosinophils, basophils and/or neutrophils such as elastase, cathepsin-G, tryptase, chymase, kinins, kallikrein, tumor necrosis factor, chymotrypsin, GEF, collagenase, inhibit IgE production and the like.

The serine protease inhibitors included in the present invention are human alpha 1-antichymotrypsin, alpha 1-antitrypsin, alpha 2-macroglobulin, eglin, elastinal 1, elastin 3, eglin 2, C-reactive protein, beta 1-antigellagenase, serine amyloid A protein, alpha cysteine protease inhibitors, inter-alpha-trypsin inhibitor, secretory leucocyte protease inhibitor, bronchial mucous inhibitor, and C-1-inhibitor. The inhibitors of the invention may be natural or prepared by recombinant means. The recombinant may be glycosylated.

The use of alpha 1-antitrypsin and alpha 1-antichymotrypsin in combination with a corticosteroid has been especially useful in the treatment of the various inflammatory skin conditions including those which are induced by autoimmune disease, virus and bacterial infections.

The inhibitors of the invention may be derived from human blood or prepared by cloning, by conventional techniques utilizing an oligonucleotide probe or antibody probe, and the like. The recombinant gene product of the invention is especially useful since it is free of contaminating viruses when produced.

The analogs, salts and derivatives may be formed utilizing conventional techniques associated with other proteins without effecting the utility of the compound. There may be prepared the alkali metal salts, acid-addition salts, and esters similar to other proteins or peptides.

The following examples further illustrate the practice of this invention, but are not intended to be limiting thereof. It will be appreciated that the selection of actual amounts of specific serine protease inhibitors and corticosteroids to be administered to any individual patient (human or animal) will fall within the discretion of the attending physician and will be prescribed in a manner commensurate with the appropriate dosages will depend on the stage of the disease and like factors uniquely within the purview of the attending physician.

The following formulations were prepared and assessed by the pharmacist and patient to determine a commerically acceptable vehicle having the best penetration. Alpha 1-antitrypsin was used as representative serine protease inhibitor because it had a common solubility and characteristic for formulation.

| Example | |
|---|---|
| FORMULA #1 | Alpha -antitrypsin ($\alpha$ 1-PI) |
| | petrolatum |
| | mineral oil |
| | mineral wax |
| | wool wax alcohol |
| | barquat |
| Pharmacist assessment: | 1. One of the methods of formulation was to incorporate the $\alpha$-1-PI powder into the ointment dry. This caused the ointment to have a grainy texture, but the Alpha-1-PI was well protected and preserved inside the ointment. This preparation worked well but the concentration needed to be at least 5% in order to get a good therapeutic response. This concentration caused the preparation to cost about $130.00 per ounce. |
| | 2. This time we hydrated the Alpha-1-PI with 7 ml water per 1 gram vial and incorporated this into the ointment maintaining 5% concentration. This preparation was smooth, looked more pleasing and spread more evenly. The therapeutic response was quicker because the $\alpha$-1-PI was pre-hydrated. |
| Patient's assessment: | The patient's didn't like the graininess of the ointment preparation from the dry powder. They generally preferred the ointment pre-hydrated but still objected to the greasy feel. |
| FORMULA #2 | $\alpha$ 1-PI |
| | calamine precipitated |
| | diphenhydramine |
| | barquat |
| Pharmacist assessment: | The dry pulverized Alpha-1-PI was added to the solution in various concentration. This preparation was messy and would soil the patient's clothing. We rejected it for this reason. |
| Patient's assessment: | The patient's felt the same way we did about the messiness of this preparation. |
| FORMULA #3 | $\alpha$ 1-PI |
| | 8-Hydroxy-Quinolone sulfate 0.3% |
| | petrolatum |
| | lanolin |
| | barquat |
| Pharmacist assessment: | The $\alpha$ 1-PI was incorporated into this ointment both wet and dry. Either preparation was pharmaceutically acceptable, but was rejected because the lanolin increased the potential for and allergic reaction. |
| Patient's assessment: | The most common remarks were in reference to the greasiness and strong odor of this preparation. |
| FORMULA #4 | $\alpha$ 1-PI |
| | water — mineral oil |
| | propylene glycol — glyceryl stearate |
| | PEG-100 stearate — PEG-40 stearate |
| | laureth-4 — PEG-4-dilaurate |
| | lanolin oil — sodium acetate |
| | carbomer-934 — trianolamine |
| | methylparaben — dioctyl Na sulfosuccinate |
| | fragrance — acetic acid |
| | — barquat |
| Pharmacist assessment: | The powdered Alpha-1-PI was added to this formula to form a smooth and soothing lotion. This preparation was a little to runny and had a very strong odor that tended to linger. This preparation was rejected for these reasons. |
| Patient's assessment: | The patient's comments were most often centered of the objectional odor. |
| FORMULA #5 | $\alpha$ 1-PI |
| | coal tar 5% |
| | hydro-alcoholic gel (13.8% alcohol) |
| | barquat |
| Pharmacist assessment: | The powdered $\alpha$-1-PI was added to this formula in various concentrations. This preparation was smelly, messy and would stain clothing. There is a possibility that the alcohol in the vehicle could be irritating and/or drying to the patient's skin and therefore undesirable. It was rejected for these reasons. |
| Patient's assessment: | This product was never assessed by a patient. |
| FORMULA #6 | $\alpha$ 1-PI |
| | water — propylene glycol |
| | mineral oil — isopropyl myristate |
| | stearic acid — glyceryl stearate |
| | PEG-100 stearate — sunflower seed oil |
| | tocopherol acetate — retinyl palmitate |
| | ergocalciferol — lanolin alcohol |
| | triethanolamine — myristyl myristate |
| | simethicone — carbomer-934 |
| | cetyl alcohol — stearyl alcohol |
| | allantoin — methylparaben |
| | quaternium-15 — propylparaben |
| | sorbic acid — fragrance |
| | — barquat |
| Pharmacist assessment: | The powered $\alpha$-1-PI was added to this formula in various concentrations. This preparation was cosmetically pleasing. It was smooth in texture and would spread evenly. The fragrance and feel gave this preparation much appeal. |
| Patient's assessment: | The patients consider this preparation quite good but the lotion was less occlusive than was needed for some of the patient's condition. |
| FORMULA #7 | $\alpha$ 1-PI |
| | urea 10% — water (scented) |
| | carbomer-940 — cetyl alcohol |
| | isopropyl palmitate — PEG-8 dioleate |
| | PEG-8 distearate — propylene glycol |
| | propy-gly diapelargonate | |
| | stearic acid — trolamine |
| | xanthan gum — fragrance |
| | barquat | |
| Pharmacist assessment: | This formulation made a very good preparation. It was smooth, pleasantly scented and occluded the skin quite well. |
| Patient's assessment: | This formula was well accepted by the patients. No negative comments noted. |
| FORMULA #8 | $\alpha$ 1-PI 5% |
| | purified water 5% — petrolatum 38.95% |
| | mineral oil 20% — mineral wax 20% |
| | wool wax alcohol 10% — barquat 0.05% |
| | metylchloroisothiazolinone-methylisothiazolinone 1% |
| Pharmacist assessment: | The dry powder was added to this preparation. There was adequate water to properly hydrate the $\alpha$-1-PI. The preparation was very smooth and spread very well. It was a little more oily than some of the other lotion. |

| | |
|---|---|
| -continued | |
| Example | |
| Patient's assessment: | This lotion was well accepted by the patients. No negative comments were recorded. |
| FORMULA #9 | α 1-PI |
| | water glycerin |
| | cetearyl alcohol palm oil glyceride |
| | ceteareth-20 mineral oil |
| | petrolatum sorbitol |
| | avocado oil glyceryl dilaurate |
| | dimethicone isopropyl palmitate |
| | stearic acid allantoin |
| | nonoxynol-9 |
| | squalene methylparaben |
| | sodium carbomer-941 propylparaben |
| | quaternium-15 fragrance |
| Pharmacist assessment: | This lotion went on smooth and vanished very quickly. No greasy feeling remained. The color and fragrance should be improved. |
| Patient's assessment: | Most patients liked the way this preparation would vanish and not leave a greasy residue. |
| FORMULA #10 | α 1-PI |
| | dimethicone 3% water |
| | petrolatum glycerin |
| | steareth-2 cetyl alcohol |
| | benzyl alcohol laureth-23 |
| | magnesium Al silicate carbomer-934 |
| | sodium hydroxide quaternium-15 |
| Pharmacist assessment: | This lotion was a little slower vanishing than some. It tended to stay wet longer than I like. This preparation did not have very much occlusion and seemed to be more of a cleansing lotion. I did not feel as if it would moisturize well enough for most of our patients. |
| Patient's assessment: | The patient did not offer any complaints on the feel of this lotion, but a few objected to the fragrance. |
| Laureth-23 could be replaced by an ethoxylated nonylphenol. | |
| FORMULA #11 | α 1-PI |
| | menthol camphor |
| | alum salicylic acid |
| | phenol fragrance |
| | petrolatum lanolin |
| | cocoa butter wax base |
| | quaternium-15 |
| Pharmacist assessment: | This preparation would absorb very little water, therefore the powder needed to be blended dry. The fragrance was strong, the menthol was cooling and it was very occlusive. This preparation may be good for some application, but it does not work well for atopic dermatitis. |
| Patient's assessment: | Most of the patients thought the fragrance was to strong and it was too greasy. |
| FORMULA #12 | α 1-PI |
| | anhydrous lanolin plain |
| | barquat |
| Pharmacist assessment: | This preparation had a strong odor and was very greasy. I feel this high concentration of lanolin may cause some patients with wool allergies to react. |
| Patient's assessment: | The odor was too strong and it was too greasy. |
| FORMULA #13 | α 1-PI |
| | deodorized cocoa butter |
| | barquat |
| Pharmacist assessment: | This preparation was firm and difficult to blend. We had to blend the powder into it dry. This preparation occluded the skin very well, but was difficult to work with. |
| Patient assessment: | This preparation was well accepted by the patients. |

| | |
|---|---|
| -continued | |
| Example | |
| FORMULA #14 | α 1-PI |
| | water mineral oil |
| | petrolatum sorbitol |
| | lanolin lanolin alcohol |
| | stearic acid triethanolamine |
| | butylparaben methylparaben |
| | propylparaben sodium chloride |
| | quaterium-15 |
| Pharmacist assessment: | This preparation was one of the better occlusive lotions. It went on smooth and made a very nice moisturizing agent. |
| Patient's assessment: | This preparation was generally well accepted by the patients. No objections were made to this lotion. |
| FORMULA #15 | α 1-PI |
| | mineral oil water |
| | propylene glycol glyceryl stearate |
| | PEG-100 stearate PEG-40 stearate |
| | PEG-4 dilaurate laureth-4 |
| | lanolin oil methylparaben |
| | propylparaben fragrance |
| | carbomer-934 triethanolamine |
| | dioctyl Na sulfosuccinate: quaternium-15 |
| Pharmacist assessment: | This preparation was a very good lotion. It went on smooth but was fluid enough to spread over large areas. It was one of the more occlusive lotions. The fragrance and texture was pleasant. |
| Patient's assessment: | This preparation was generally well accepted by the patients. No negative comments were noted. |
| FORMULA #16 | α 1-PI |
| | water mineral oil |
| | lactic acid sodium PCA |
| | isopropyl palmitate stearyl alcohol |
| | ceteareth-20 sodium hydroxide |
| | glyceryl stearate PEG-100 stearate |
| | myristyl lactate cetyl alcohol |
| | carbomer-940 DMDM hydantoin |
| | fragrance methylparaben |
| | propylparaben quaternium-15 |
| Pharmacist assessment: | This preparation was very slow to vanish. One would have to rub the area much longer than with other lotion. The occlusion was not as good as some of the other lotions. Fragrant was pleasant and texture smooth. |
| Patient's assessment: | This preparation was generally accepted well. The only complaint was the messiness during to slow absorption when applied. |
| FORMULA #17 | α 1-PI |
| | Na Chloride 0.65% Na phosphate |
| | polyethylene glycol sucrose quaterium-15 |
| Pharmacist assessment: | A fine mist sprayer was used to apply this solution. It was easy to apply and could cover large or badly abraded areas. After the solution dried one would need to occlude the area with an ointment or lotion. The advantage to this system is less α 1-PI was needed to get the desired therapeutic effect. |
| Patient's assessment: | The patients were able to apply the Alpha-1-PI using this method without much trouble. Some did not like using two procedures to apply the drug. Patients with very sore hands had some difficulties working the sprayer. |
| FORMULA #18 | α 1-PI |
| | sterile water Na chloride |
| | Na phosphate polyethyleneglycol |
| | sucrose quaternium-15 |
| Pharmacist assessment: | A fine mist sprayer was used to apply |

| Example | |
|---|---|
| | this solution. It was easy to apply and could cover large and badly abraded areas. After the solution dried one would need to occlude the area with an ointment or lotion. The advantage to this system is less α 1-PI was needed to get the desired therapeutic effect. |
| Patient's assessment: | The patients were able to apply the α 1-PI using this method without much trouble. Some did not like using two procedures to apply the drug. Patients with very sore hands had some difficulties working the sprayer. |
| FORMULA #19 | α 1-PI<br>NaCl 0.65%   Na phosphate<br>benzyl alcohol 1%   sucrose<br>polyethylene glycol   quaternium-15 |
| Pharmacist assessment: | A fine mist sprayer was used to apply this solution. It was easy to apply and could cover large or badly abraded areas. After the solution dried one would need to occlude the area with an ointment or lotion. The advantage to this system is less Alpha-1-PI was needed to get the desired therapeutic effect. The benzyl was added as a preservative. |
| Patient's assessment: | The patients were able to apply the Alpha-1-PI using this method without much trouble. Some did not like using two procedures to apply the drug. Patients with very sore hands had some difficulties working the sprayer. Some of the patients complained that this solution would burn or irritate the skin. We determined this problem was due to the benzyl alcohol. |
| FORMULA #20 | α 1-PI<br>hydroxypropyl methylcellulose 2910 1%<br>benzalkonium cl. 0.01%<br>diabasic sodium phosphate<br>monobasic sodium phosphate<br>sodium citrate<br>sodium chloride |

| Example | |
|---|---|
| | purified water |
| Pharmacist assessment: | This preparation was used as a drop application. The solution was easy to apply and would spread easily. It took only a minute or so for the solution to dry. We did not intend to occlude with an ointment. The solution seemed to cause some drying of the area when applied. Therapeutic effect was still good in spite of the drying. |
| Patient's assessment: | It was easy to use. Some of the patients did not like the drying effect of this preparation. |
| FORMULA #21 | α 1-PI<br>polyvinyl alcohol 1.4%   povidone 0.6%<br>chlorobutanol 0.5%   purified water<br>sodium chloride NaOH or HCl for pH<br>barquat |
| Pharmacist assessment: | This preparation was used as a drop application. The solution was easy to apply and would spread easily. It took only a minute or so for the solution to dry. We did not intend to occlude with an ointment. The solution seemed to cause some drying of the area when applied. |
| Patient's assessment: | It was easy to use. Some of the patient's did not like the drying effect of this preparation. |

It did not appear to make any difference as to the vehicle utilized for the quaternary ammonium salt to aid in penetration of α 1-PI.

We claim:

1. In a pharameceutical composition for the topical treatment of a mammal having a skin disease in which said composition contains an effective amount of α-1-antitrypsin and a non-aqueous lipid miscible carrier the improvement which comprises said composition containing an effective amount of benzalkonium chloride at an effective concentration for increasing the chemical stability and, penetration of said protease inhibitor in the skin.

* * * * *